US010201383B2

(12) United States Patent
Ogata et al.

(10) Patent No.: US 10,201,383 B2
(45) Date of Patent: Feb. 12, 2019

(54) METHODS FOR TISSUE ABLATION MEASUREMENT AND CONTROL AND DEVICES THEREOF

(71) Applicant: RetroVascular, Inc., Pleasanton, CA (US)

(72) Inventors: Wayne Ogata, San Ramon, CA (US); Xiang Ian Gu, Foster City, CA (US); Steven Meyer, Oakland, CA (US); Alireza Yavari, Sunnyvale, CA (US)

(73) Assignee: Retrovascular, Inc., Pleasanton, CA (US)

( * ) Notice: Subject to any disclaimer, the term of this patent is extended or adjusted under 35 U.S.C. 154(b) by 539 days.

(21) Appl. No.: 14/216,849

(22) Filed: Mar. 17, 2014

(65) Prior Publication Data

US 2014/0309632 A1    Oct. 16, 2014

Related U.S. Application Data

(60) Provisional application No. 61/800,886, filed on Mar. 15, 2013.

(51) Int. Cl.
*A61B 18/12*    (2006.01)
*A61B 18/14*    (2006.01)
(Continued)

(52) U.S. Cl.
CPC ...... *A61B 18/1233* (2013.01); *A61B 18/1492* (2013.01); *A61B 2017/00057* (2013.01); *A61B 2017/00106* (2013.01); *A61B 2018/00642* (2013.01); *A61B 2018/00678* (2013.01); *A61B 2018/00702* (2013.01);
(Continued)

(58) Field of Classification Search
CPC ............................................ A61B 2018/00636
See application file for complete search history.

(56) References Cited

U.S. PATENT DOCUMENTS 4,860,745 A    8/1989    Farin et al.
5,318,563 A *  6/1994    Malis .................... A61B 18/12
                                                    606/34
(Continued)

OTHER PUBLICATIONS

International Preliminary Report on Patentability, corresponding to PCT/US2014/030751, dated Sep. 24, 2015.
(Continued)

*Primary Examiner* — Ronald Hupczey, Jr.
(74) *Attorney, Agent, or Firm* — LeClairRyan PLLC

(57) ABSTRACT

An apparatus comprises a first longitudinal member and a second longitudinal member configured to be located near a tissue region. An energy source is coupled to first longitudinal member and second longitudinal member. A measuring device is configured to measure at least one characteristic of the tissue region. An energy controller is coupled to the energy source and the measuring device. The energy controller includes a processor coupled to a memory and configured to execute programmed instructions stored in the memory, comprising initiating a delivery of energy to the tissue region from the energy source. One or more items of data are received from the measuring device based on the delivery of energy to the tissue region. The delivery of energy to the tissue region is adjusted based on the one or more items of data.

32 Claims, 6 Drawing Sheets

(51) Int. Cl.
*A61B 17/00* (2006.01)
*A61B 18/00* (2006.01)

(52) U.S. Cl.
CPC .............. *A61B 2018/00708* (2013.01); *A61B 2018/00779* (2013.01); *A61B 2018/00785* (2013.01); *A61B 2018/00791* (2013.01); *A61B 2018/00827* (2013.01); *A61B 2018/00869* (2013.01); *A61B 2018/00875* (2013.01); *A61B 2018/00892* (2013.01)

(56) References Cited

U.S. PATENT DOCUMENTS

| | | | |
|---|---|---|---|
| 5,893,848 A * | 4/1999 | Negus | A61B 18/00 606/1 |
| 6,796,981 B2 | 9/2004 | Wham et al. | |
| 6,813,515 B2 * | 11/2004 | Hashimshony | A61B 5/0507 324/632 |
| 7,232,437 B2 * | 6/2007 | Berman | A61B 18/22 600/374 |
| 7,828,793 B2 * | 11/2010 | Thompson | A61B 18/08 606/29 |
| 8,333,759 B2 * | 12/2012 | Podhajsky | A61B 18/1206 606/34 |
| 2002/0026188 A1 | 2/2002 | Balbierz et al. | |
| 2008/0208185 A1 | 8/2008 | Fischer et al. | |
| 2009/0082765 A1 | 3/2009 | Collins et al. | |
| 2010/0262135 A1 | 10/2010 | Berube | |
| 2012/0016359 A1 * | 1/2012 | Podhajsky | A61B 18/1206 606/34 |
| 2012/0296262 A1 * | 11/2012 | Ogata | A61B 18/1492 604/20 |

OTHER PUBLICATIONS

International Search Report, corresponding to PCT/US2014/030751, dated Sep. 5, 2014.
European Search Report for corresponding EP Application No. 14765833.0, dated Aug. 4, 2016, pp. 1-7.
China Office Action for corresponding China Application No. 201480015486.4, Jun. 28, 2017, pp. 1-12.
Office Action for corresponding Chinese Patent Application No. 201480015486.4, dated Mar. 23, 2018, pp. 1-10.

* cited by examiner

METHODS FOR TISSUE ABLATION MEASUREMENT AND CONTROL AND DEVICES THEREOF

This application claims the benefit of U.S. Provisional Application Ser. No. 61/800,886, filed Mar. 15, 2013, which is hereby incorporated by reference in its entirety.

FIELD

This technology generally relates to methods and devices monitoring and controlling energy delivery to a tissue region and, more specifically, to methods and devices for tissue ablation measurement and control.

BACKGROUND

Chronic total occlusion (CTO) is the complete blockage of a vessel and may have serious consequences if not treated in a timely fashion. The blockage could be due to atheromatous plaque or old thrombus.

One of the common procedures for treating CTOs of the coronary arteries is percutaneous transluminal coronary angioplasty (PTCA). During a PTCA procedure, a small incision is typically made in the groin. A guiding catheter over a guidewire is introduced into the femoral artery and advanced to the occlusion. At times, with gentle maneuvering, the guidewire is able to cross the occlusion. A balloon-tipped angioplasty catheter is then advanced over the guidewire to the occlusion. The balloon is inflated, separating or fracturing the atheroma. Often times, a stent is subsequently or simultaneously deployed.

Some of the common steps involved in the PTCA procedure for CTOs are the simultaneous injection of a contrast agent in the contra-lateral vessel, securing backup force or stabilization for a guidewire (which could invoke additional personnel to handle the catheter), puncturing the plaque, or drilling or rotating the guidewire to push it through the dense plaque by way of example only. Because of the stiff resistance sometimes offered by dense plaque, one could be forced to use stiff wires. Occasionally, the wires could puncture the vessel wall calling for remedial measures.

The most common percutaneous coronary intervention (PCI) failure mode for CTOs is inability to successfully pass a guidewire across the lesion into the true lumen of the distal vessel. To date, there is no consensus on how best to treat CTO after attempts with conventional guidewires have failed. Different strategies for CTOs have been developed including the side branch technique, the parallel wire technique, and the IVUS guided technique. Mechanical and energy based devices have also been proposed for passing guidewires through hard calcified occlusions, such as mechanical cutting or oscillation and laser or ultrasound or radiofrequency (RF) energy ablation. Each of these devices works by strictly utilizing an antegrade approach and locally applying energy (typically in the form of heat) at the tip of the guidewire or catheter device in order to create a channel and hopefully enter the distal true lumen.

RF energy is widely used to coagulate, cut, or ablate tissue. In both monopolar and bipolar modalities, conductive electrodes contact the tissue to be treated. In the monopolar mode, the active electrode is placed in contact with the tissue to be treated and a return electrode with a large surface area is located on the patient at a distance from the active electrode. In the bipolar mode, the active and return electrodes are in close proximity to each other bracketing the tissue to be treated. Sometimes an array of electrodes is used to provide better control over the depth of penetration of the RF field and hence control over the temperatures to which the tissue is heated.

There are many disadvantages with both monopolar and bipolar modalities. For example, in the monopolar arrangement, because of the large physical separation between the electrodes there are frequent reports of local burning at the electrode sites. This would clearly be undesirable where one of the electrodes will be inside a blood vessel. The other serious issue is the likelihood of forming blood clots. The tissue that is in contact with the electrodes can be coagulated or ablated. In the case of the electrodes being present inside a blood vessel, the formation of dangerous blood clots would obviously be undesirable.

In an attempt to overcome the issues described above, various device and electrode configurations are described in the following patents. U.S. Pat. Nos. 5,366,443 and 5,419,767 describe the use of RF electrodes on a catheter to cross a lesion. These patents describe a bipolar electrode assembly at the distal tip of a catheter that is in contact with the occlusion, and that the application of RF energy ablates the occlusion and renders the occlusion susceptible for the guidewire to penetrate. This method has the drawback that careful tracking of the occlusion and the ablation process is necessary to avoid trauma to the vessel walls or healthy tissue, since the possibility of short-circuiting of current through healthy tissue instead of the occlusion is high. U.S. Pat. No. 5,419,767 overcomes this limitation to a certain extent through the use of a multiple electrode array. However, this device requires a channel to be pre-created through the occlusion so that the device can be passed through a guidewire traversing this channel, which is not always easy.

U.S. Pat. No. 5,514,128 describes a laser catheter device that enables ablation of an occlusion in the vasculature. This system has similar drawbacks to the ones described above, i.e., the need for a guidance system, potential for healthy tissue to be ablated, and complexity (and hence cost) of the device.

One major problem with the existing devices is the potential for the ablation energy to damage the walls of the vasculature, in the absence of a mechanism to track the orientation and position of the energy delivery member. Several devices exist in the prior art that address the issue of tracking and steering of the energy delivery element. U.S. Pat. No. 6,911,026 describes a magnetic steering and guidance system to direct an ablation device that delivers RF energy at the tip in a unipolar configuration where the return electrode is placed externally in contact with the body or in a bipolar configuration where the return electrode is a ring surrounding the central wire electrode.

U.S. Pat. No. 6,416,523 discusses a mechanical cutting device where the guidance is provided by measuring impedance of the tissue in contact. The guidance system senses the difference in impedance between the stenotic tissue and the vessel wall and directs the cutting element to the occlusion.

However, none of these alternate strategies have provided satisfactory results for the most challenging of CTOs. In the case of hard calcified occlusions, the revascularization procedure can be tedious and time consuming. Therefore, there is a need for improved methods of ablating or disrupting the occlusive material that are safe, efficacious and fast. It would be beneficial to have alternate techniques and devices that would recanalize a CTO without the shortcomings of the current techniques.

CTOs that are hard to recanalize, either because of the tortuous anatomy of the diseased vessel, or because the proximal end of the stenosis is too hard for the guide wire to penetrate, or other characteristics of the CTO that would make the standard procedure vulnerable to failure would benefit from newer approaches to recanalize CTOs. Recently a combined antegrade-retrograde approach has been proposed for recanalizing chronic occlusions U.S. application Ser. No. 11/706,041, which is hereby incorporated by reference herein in its entirety. The method disclosed in the co-pending application would benefit from the use of energy for crossing CTOs.

SUMMARY

An apparatus comprises a first longitudinal member and a second longitudinal member configured to be located near a tissue region. An energy source is coupled to first longitudinal member and second longitudinal member. A measuring device is configured to measure at least one characteristic of the tissue region. An energy controller is coupled to the energy source and the measuring device. The energy controller includes a processor coupled to a memory and configured to execute programmed instructions stored in the memory, comprising initiating a delivery of energy to the tissue region from the energy source. One or more items of data are received from the measuring device based on the delivery of energy to the tissue region. The delivery of energy to the tissue region is adjusted based on the one or more items of data.

A method comprises initiating, by a tissue ablation monitoring computing device, a delivery of energy from an energy source to a tissue region through a first longitudinal member and a second longitudinal member located near the tissue region. One or more items of data are received from a measuring device based on the delivery of energy to the tissue region. The delivery of energy to the tissue region is adjusted based on the one or more items of data.

This technology provides a number of advantages including providing safe and effective methods and devices for tissue ablation measurement and control that allow for monitoring the state of the tissue ablation and adjusting the energy delivered to more effectively perform the tissue ablation process.

DETAILED DESCRIPTION

Figure 1:
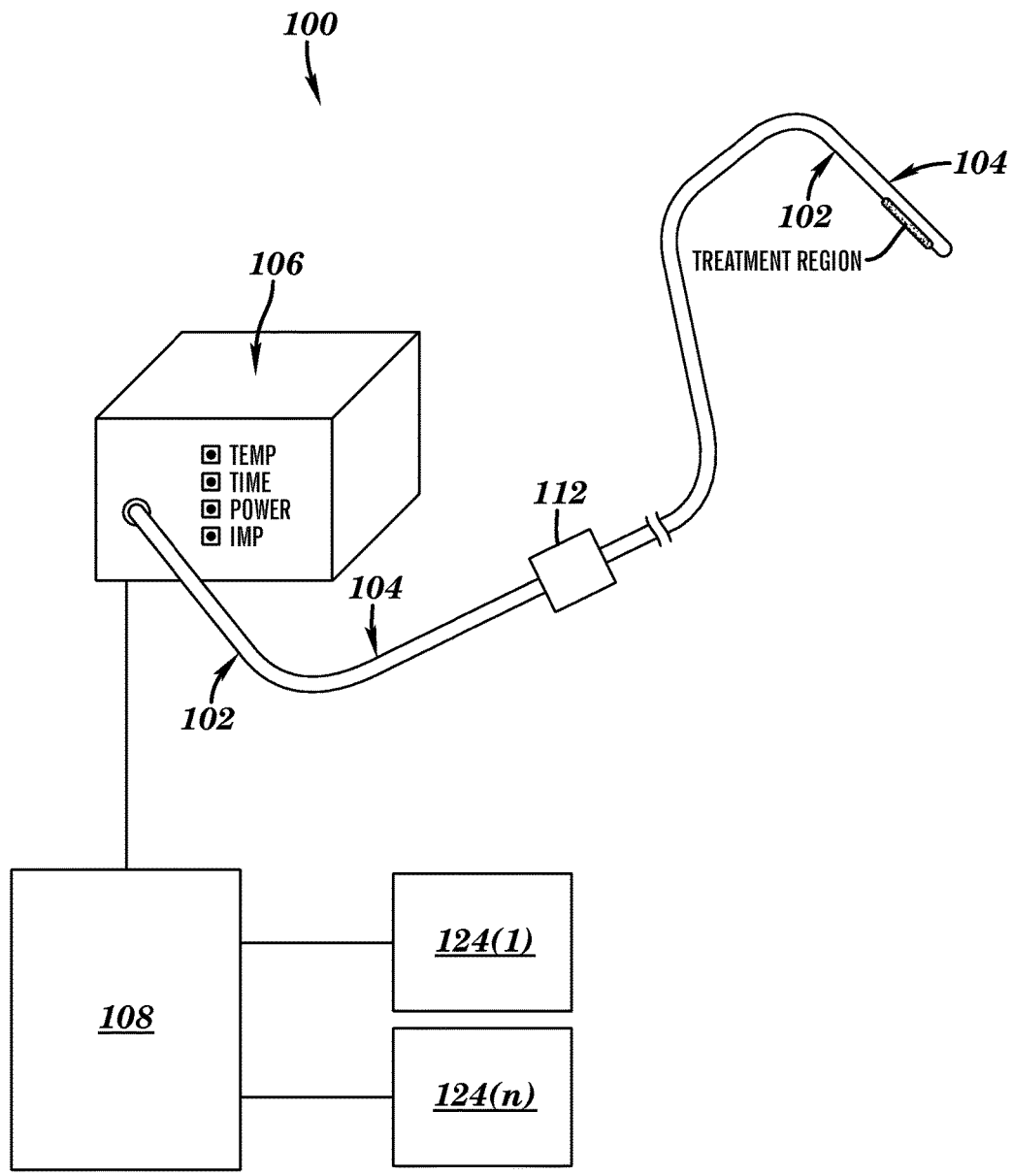
FIG. 1 is a partial perspective view and partial block diagram of an example of an apparatus for tissue ablation measurement and control.
Figure 2:
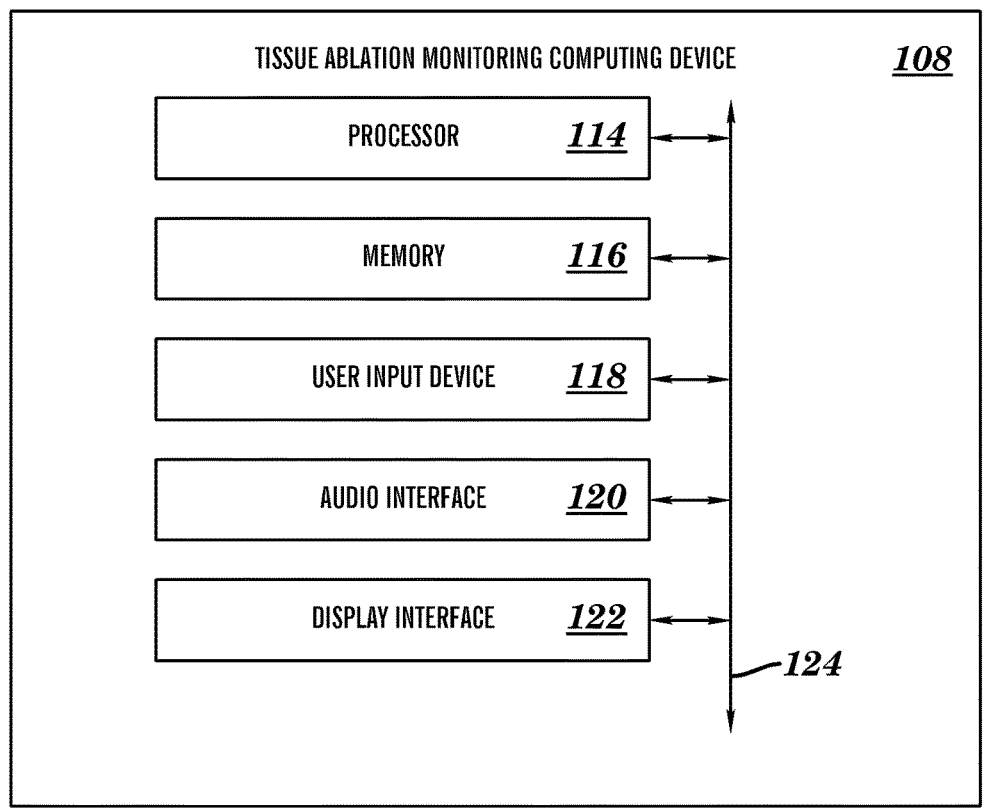
FIG. 2 is a block diagram of an example of the tissue ablation computing device shown in FIG. 1.

An exemplary tissue ablation measurement and control apparatus 100 is illustrated in FIGS. 1-2. The tissue ablation measurement and control apparatus 100 includes a first longitudinal member 102, a second longitudinal member 104, an energy source 106, a tissue ablation monitoring computing device 108, and a measurement device 110, although the tissue ablation measurement and control apparatus 100 could include other types and numbers of devices, components and/or other elements in other configurations. This exemplary technology provides a number of advantages including providing more efficient methods of tissue ablation measurement and control.

Referring more specifically to FIGS. 1-2, the tissue ablation measurement and control apparatus includes a first longitudinal member 102 and a second longitudinal member 104 which are configured to be advanced into the body of a patient and located near an occlusion in a tissue region. In this example, the first longitudinal member 102 and the second longitudinal member 104 are guidewires, although other types and/or numbers of longitudinal member that can be inserted into the body, such as by way of example only catheters, microcatheters, dilating catheters, or probes, may be utilized. The tissue region may be any portion of a tissue of the patient, such as various organs, body lumens or cavities, such as various ducts or vessels, or blood vessels by way of example only, comprising one or more occlusions. In one example, the first longitudinal member 102 serves as an antegrade member configured to approach the tissue region in an antegrade fashion and the second longitudinal member 104 serves as a retrograde member configured to approach the tissue region in a retrograde fashion, although the antegrade/retrograde approach is optional and the first longitudinal member and the second longitudinal member may be placed near to the tissue region using various approaches and orientations.

The first longitudinal member 102 and second longitudinal member 104 are coupled to an energy source 106, such as an RF energy or pulse generator configured to generate pulsed signals for recanalizing occluded vessels by delivering energy, such as RF energy, to the occlusion, although other types and/or numbers of energy sources could be used. The use of energy, such as radiofrequency energy, to ablate a tissue region, such as an occlusion that resides within a vessel to recanalize the vessel, has been described by way of example in the co-pending and commonly owned U.S. patent application Ser. Nos. 12/680,500 and 12/753,844, where are hereby incorporated by reference herein in their entirety. The energy source 106 is further configured to be connectable to the first and second longitudinal members 102 and 104 through a coupler 112. In one example, the coupler 112 connects at one end to the energy source 106 and at its other end to at least one of the first longitudinal member 102 and the second longitudinal member 104 to provide RF energy from the energy source 106 to the first and second longitudinal members 102 and 104, although the longitudinal members 102 and 104 may be connected to the energy source 106 in other manners. In one example, the coupler 112 is a torque device that transmits signals from the energy source 106 to the longitudinal members 102 and 104, although other types and/or numbers of couplers may be utilized.

The tissue ablation monitoring computing device 108 serves as an energy controller and is configured to be connectable to the energy source 106, although the energy source 106 may be located in the same unit as the tissue ablation monitoring computing device 108. Referring now to FIG. 2, the tissue ablation monitoring computing device 108, includes at least one processor 114, a memory 116, a user input device 118, an audio interface 120, and a display interface 122, which are coupled together by a bus 124 or other link, although other types and/or numbers of systems, devices, components, parts, and/or other elements in other configurations and locations can be used. The processor 114 in the tissue ablation monitoring computing device 108 executes a program of stored instructions for one or more aspects of the present invention as described and illustrated by way of the examples herein, although the processor 114 could execute other types and/or numbers of programmed instructions.

The memory 116 in the tissue ablation monitoring computing device 108 stores these programmed instructions for one or more aspects of the present invention as described and illustrated herein, although some or all of the programmed instructions could be stored and/or executed elsewhere. A variety of different types of memory storage devices, such as a random access memory (RAM) or a read only memory (ROM) in the system or a floppy disk, hard disk, CD ROM, DVD ROM, or other computer readable medium which is read from and/or written to by a magnetic, optical, or other reading and/or writing system that is coupled to the processor 114, can be used for the memory 116 in the tissue ablation monitoring computing device 108.

The user input device 118 in the tissue ablation monitoring computing device 108 can be used to input selections, such as a one or more parameters related to the tissue ablation process by way of example, although the user input devices could be used to input other types of requests and data. The user input device 118 can include one or more keyboards, keypads or touch screens, although other types and/or numbers of user input devices can be used. The audio interface 120 is arranged to produce and receive audio signals. For example, audio interface 120 may be coupled to a speaker to generate an audio acknowledgement or alert. The display 122 in the tissue ablation monitoring computing device 108 can be used to show data and information to the user. The display 122 may be a liquid crystal display (LCD), gas plasma, light emitting diode (LED), or any other type of display used with a computing device. The display 122 may also include a touch sensitive screen arranged to receive input from an object such as a stylus or a human hand.

Although an example of the tissue ablation monitoring computing device 108 is described and illustrated herein, the tissue ablation monitoring computing device 108 can be implemented on any suitable computer apparatus or computing device. It is to be understood that the apparatuses and devices of the examples described herein are for exemplary purposes, as many variations of the specific hardware and software used to implement the examples are possible, as will be appreciated by those skilled in the relevant art(s).

Furthermore, each of the devices of the examples may be conveniently implemented using one or more general purpose computers, microprocessors, digital signal processors, and micro-controllers, programmed according to the teachings of the examples, as described and illustrated herein, and as will be appreciated by those ordinary skill in the art.

The examples may also be embodied as one or more non-transitory computer readable medium having instructions stored thereon for one or more aspects of the present invention as described and illustrated by way of the examples herein, as described herein, which when executed by a processor, cause the processor to carry out the steps necessary to implement the methods of the examples, as described and illustrated herein.

Referring again to FIG. 1, the tissue ablation monitoring computing device 108 is coupled to and configured to receive data from one or more measurement devices 124(1)-124(*n*). In one example, one of the one or more measurement devices 124(1)-124(*n*) is an electrical device configured to measure one or more electric characteristics such as current, voltage, forward power, reverse power, phase angle, and/or impedance. The one of the one or more measurement devices 124(1)-124(*n*) may be, by way of example only, an oscilloscope, LCR meter, an ammeter, a multimeter, and/or a galvanometer or another device capable of measuring and/or analyzing one or more electric characteristics. Additionally, tissue ablation monitoring computing device 108 may be optionally configured to receive data from one of the one or more measurement devices 124(1)-124(*n*) which is a physiological measuring device. In one example, the one of the one or more measurement devices 124(1)-124(*n*) is configured to measure the impedance of the tissue region, although the physiological measurement device may measure other types and/or numbers of physiological measurements, such as by way of example only temperature, pressure, composition, and/or elasticity of the tissue region. Tissue ablation monitoring computing device 108 may also be optionally configured to receive data from one of the one or more measurement devices 124(1)-124(*n*) which is a visual measurement device, such as intravascular ultrasound (IVUS), optical coherence tomography (OCT), optical coherence reflectometry (OCR), and angiography, although other types and/or numbers of visual measurement devices may be utilized.

Figure 3:
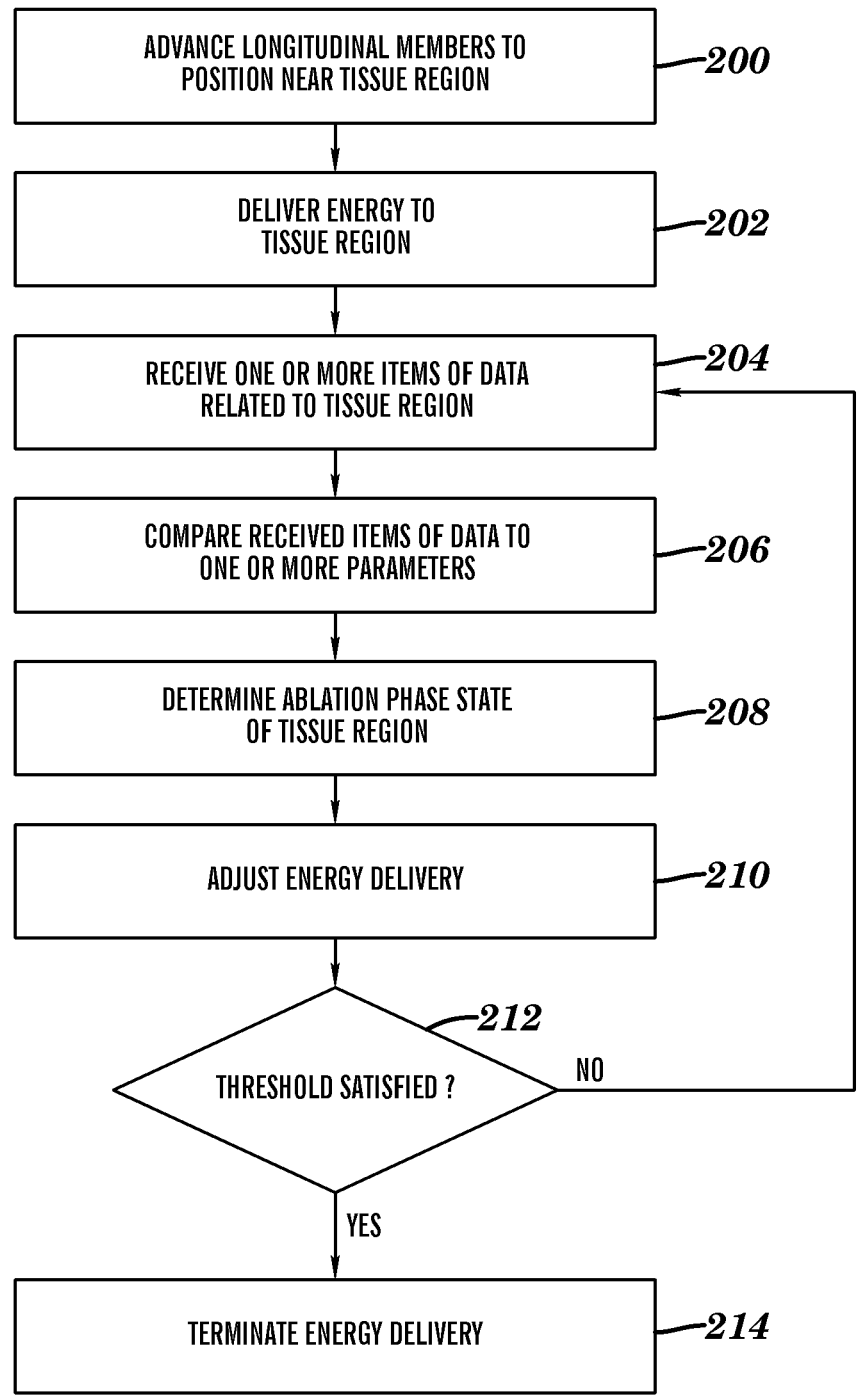
FIG. 3 is a flow chart for an example of a method of tissue ablation measurement and control.

An example of a method for tissue ablation measurement and control will now be described with reference to FIGS. 1-6. Referring more specifically to FIG. 3, an exemplary method for measuring, monitoring, and controlling tissue ablation is illustrated. In step 200, the first longitudinal member 102 and the second longitudinal member 104 are inserted into the body of the patient and located near a target tissue region. The tissue region may be any portion of a tissue of the patient such as, by way of example only, various organs, body lumens or cavities, such as various ducts or vessels, or blood vessels comprising one or more occlusions. In one example, the first longitudinal member 102 serves as an antegrade member configured to approach the tissue region in an antegrade fashion and the second longitudinal member 104 serves as a retrograde member configured to approach the tissue region in a retrograde fashion, although the antegrade/retrograde approach is optional and the first longitudinal member and the second longitudinal member may be placed relative and near to the tissue region using various approaches and orientations.

Next, in step 202, an energy delivery is initiated from the energy source 106 to the tissue region through the first longitudinal member 102 and second longitudinal member. The energy delivery is initiated by the tissue ablation monitoring computing device 108, although the energy delivery may be initiated in other manners, such as directly by a user with a switch by way of example. In one example, energy is applied as a square-wave at a frequency between 200 KHz to 2 MHz for a duration between 1 second to 20 seconds using a pulse duration between 20 ns to 20 ms and a pulse period between 20 μs to 2 seconds, although the energy may be applied in other manners at other parameters.

In step 204, the tissue ablation monitoring computing device 108 receives one or more items of data related to the tissue ablation from one or more of the measurement devices 124(1)-124(*n*), although the tissue ablation monitoring computing device 108 may receive other items of data from other locations and devices. The one or more items of data may be related to electrical, physiological, or visual measurements from the measurement devices 124(1)-124(*n*).

Next, in step 206, the tissue ablation monitoring computing device 108 optionally compares the received one or more items of data to one or more parameters related to the one or more items of data. The one or more parameters may be, by way of example only, one or more pre-configured parameters or protocols, such as specific tissue ablation waveforms, stored in the memory 116. Alternatively, the one or more parameters may be input by a user and include values, such an input voltage, input current, maximum voltage, maximum current, maximum temperature, impedance, treatment time, power level, or a combination of these or other parameters by way of example.

In step 208, the tissue ablation monitoring computing device 108 optionally determines a phase state of the tissue ablation process based on the received one or more items of data. The phase state of tissue ablation may be determined by way of example by voltage and/or current waveforms received from one or more of the measuring devices 124(1)-124(n). The tissue ablation monitoring computing device 108 is configured to process the measurements obtained from the one or more measurement devices 124(1)-124(n) during the ablation treatment. In one example, the processor 114 determines the phase of the ablation treatment by comparing the obtained electrical measurement with data related to one or more waveform patterns stored in the memory 116 using various algorithms known in the art.

Figure 4:
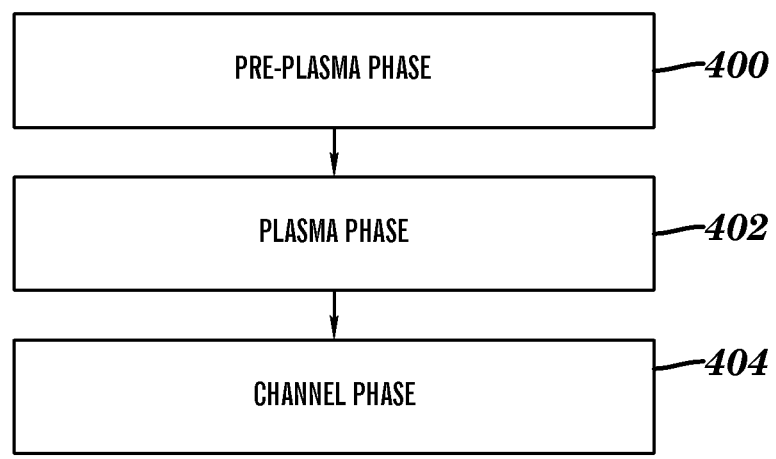
FIG. 4 is a flow chart of an exemplary sequence of tissue ablation.

Referring now to FIG. 4, an exemplary sequence of tissue ablation is shown. At step 400, following an activation of the energy at the spaced apart ends of each of the longitudinal members 102 and 104 near the tissue region, a pre-plasma phase occurs where the surrounding material, such as the tissue or fluid near treatment region by way of example, can be vaporized to form bubbles, and ionization activities can take place in this region that further lead to plasma discharge in step 402.

At step 402, a plasma phase occurs whereby plasma is formed around the spaced apart ends of each of the longitudinal members 102 and 104. In one example, after sufficient voltage has been applied to the longitudinal members 102 and 104 for a sufficient duration to overcome the dielectric and/or impedance characteristics of the tissue region, electrical breakdown occurs resulting in spark discharge. During the plasma phase 402, the plasma discharge results in tissue ablation, particularly between the spaced apart ends of each of the two longitudinal members 102 and 104. In one example, the plasma discharge created during the plasma phase 402 can be viewed as the result of dielectric-barrier discharge (DBD) where the two longitudinal members create electrical discharges separated by the tissue region which acts as a quasi-dielectric barrier subjected to thermal, mechanical, and chemical influences by the plasma discharge. At step 404, a channel phase in entered after sufficient tissue ablation occurs such that the tissue breakdown results in a channel across the tissue between the spaced apart ends of each of the two longitudinal members 102 and 104.

Figure 5:
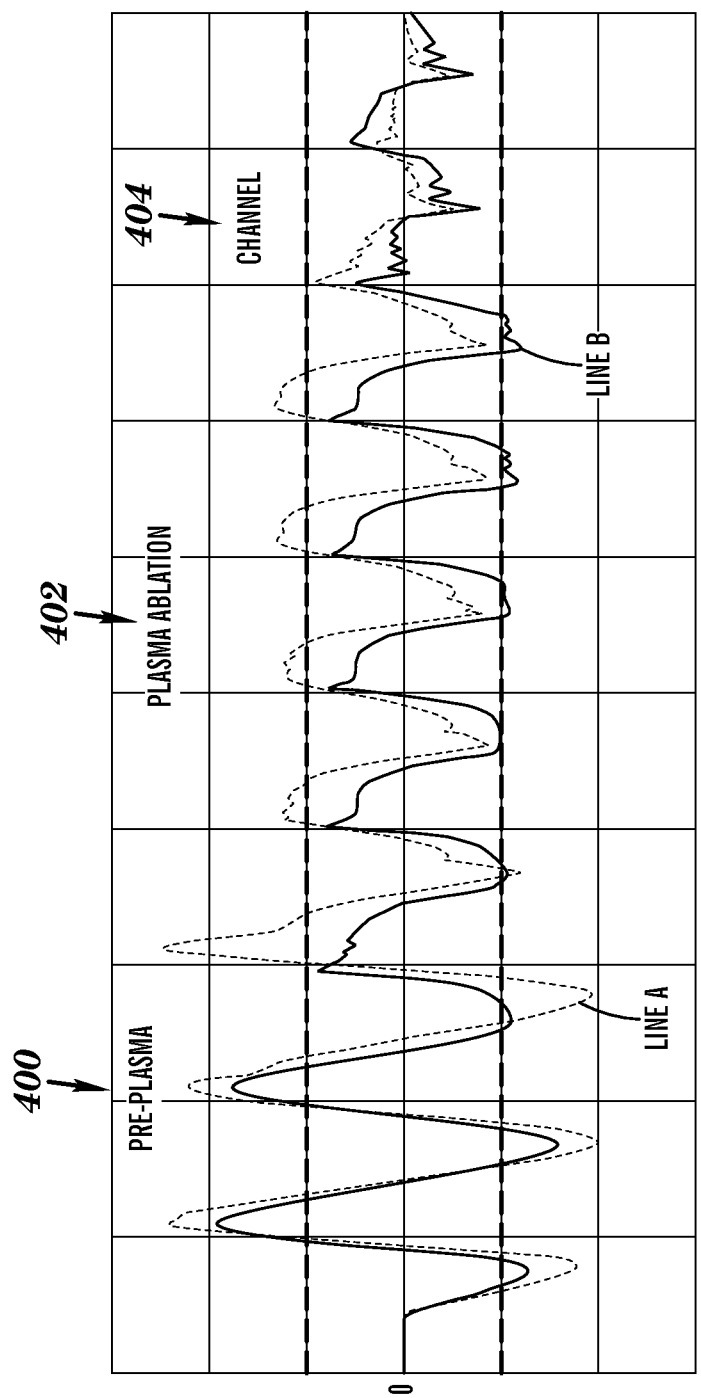
FIG. 5 is a graph of an example of a voltage waveform during three different phases of an exemplary ablation.

Referring now to FIG. 5, a screen shot of voltage representation of the tissue ablation as measured at the first longitudinal member 102 and the second longitudinal member 104 are exemplarily shown. As seen in FIG. 5, cycle-by-cycle voltage across the first longitudinal member 102 and the tissue is represented as line A and inverted cycle-by-cycle voltage across the second longitudinal member 104 and the tissue is represented as line B. The steps in the sequence of tissue ablation as described in FIG. 4 can be observed or inferred from the voltage representation. Three distinctive voltage cycle phases are observed in FIG. 5, where section 400 indicates the pre-plasma phase, where the measured voltage is observed at its highest. In one exemplary condition, peak-to-peak voltage is approximately 4000 VAC. During section 402, which indicates the plasma phase, a change in the waveform is observed and measured voltage begins to decrease, corresponding to the lower impedance during the plasma discharge. In one exemplary condition, peak-to-peak voltage is approximately 2400 VAC. During section 404, the measured voltage further decreases which indicates the channel phase. In one exemplary condition, the average energy delivered was on the order of 1.5 J/second. It should be noted that distinct changes in the waveform also occur during each phase.

Figure 6:
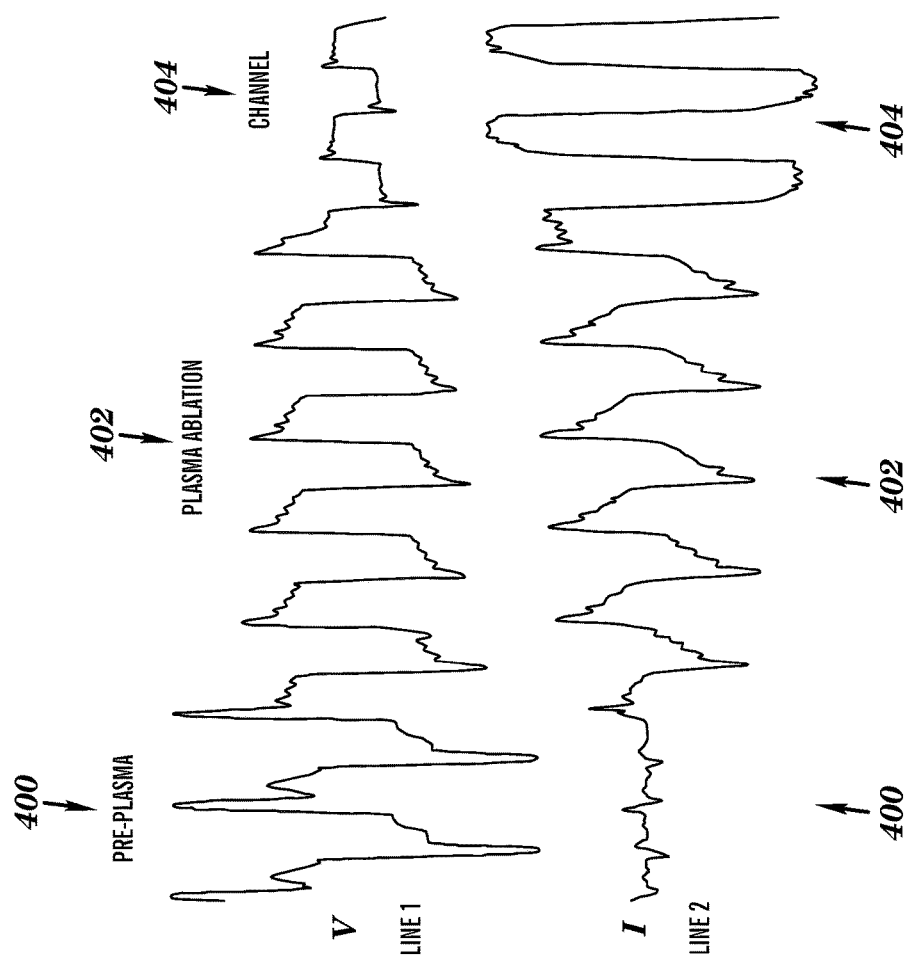
FIG. 6 is a graph of examples of voltage and current waveforms during the phases of an exemplary ablation.

Referring now to FIG. 6, two exemplary waveforms indicating tissue ablation during an animal trial are illustrated. As seen in FIG. 6, the voltage measurement is indicated as line 1 and the current measurement is indicated as line 2. As seen in FIG. 6, the pre-plasma phase 400, the plasma phase 402, and the channel phase 404 are indicated by distinct changes in the waveforms. As seen in FIG. 6, during the channel phase 404, the measured voltage decreases when comparing to the voltage measured during the plasma phase 402.

Likewise for line 2, during the channel phase 404, the current increases when compared to the current measured during plasma phase 402. In one exemplary condition, peak current is on the level of a few hundred milliamperes to a few amperes. It is further contemplated that waveforms of various patterns, amplitudes, wavelengths, and/or periods by way of example, may be observed depending on the type of energy used, electrical characteristics of the energy source, the anatomy of the tissue region, the distance between the two longitudinal members 102 and 104, the types of tissue being treated such as resistance of the tissue, or the like.

In one example, the tissue ablation monitoring computing device 108 is configured to produce a visual indication based on the determined phase of the ablation. For example, based on the measured and processed voltage data, if it is determined that the plasma phase has been achieved, an indication may be displayed on the display unit 122. The indication may be an image, an animation, or the like. Additionally, or alternatively, an audio indication may be produced via the audio interface 120.

Referring back to FIG. 3, in step 210, the tissue ablation monitoring computing device 108 adjusts the delivery of energy to the tissue region from the energy source 106. In one example, the tissue ablation monitoring computing device 108 is configured to adjust the energy delivery from the energy source 106 to the longitudinal members 102 and 104 based on the comparison to the one or more pre-configured parameters or protocols, such as specific tissue ablation waveforms, stored in the memory 116 performed in step 206.

In another example, the tissue ablation monitoring computing device 108 is configured to adjust the energy delivery from the energy source 106 to the longitudinal members 102 and 104 based directly on one or more measurements obtained from the one or more measurement devices 124(1)-124(n) based on the measurement values obtained in real-time. Alternatively, the tissue ablation monitoring computing device 108 may be configured to allow a user to set one or more parameters and control the energy from the energy source based on, at least in part, a user input. For example, the user may control or set the input voltage, input current, maximum voltage, maximum current, maximum temperature, impedance, treatment time, or power level, or a combination of these or other parameters. It is further contemplated that the tissue ablation monitoring computing device 108 may be configured to monitor and adjust the energy delivery from the energy source 106 based on a combination of the above described examples.

In another example, the tissue ablation monitoring computing device 108 is configured to prompt a user input regarding one or more treatment parameters. For example, a user may select a tissue type to be ablated, the anticipated size of the occlusion, and/or the degree of ablation desired by way of example only. Based on the user input, the tissue ablation monitoring computing device 108 is configured to select the appropriate data related to one or more pre-determined waveform patterns.

In one example, the tissue ablation monitoring device 108 is configured to control energy delivery based on data related to one or more pre-determined waveform patterns. For example, based on the data related to one or more pre-determined waveform patterns, the computer executable instructions can cause the tissue ablation monitoring computing device 108 to apply a voltage level that is configured to substantially minimize the treatment time needed to achieve plasma generation as observed in the plasma phase and thereby minimizing the duration of and the thermal effects during the pre-plasma phase.

In step 212, the tissue ablation monitoring computing device 108 determines whether a threshold measurement has been exceeded. By way of example, as previously described, the tissue ablation monitoring computing device 108 may be configured to determine whether the measurement exceeds a threshold value that indicates a change in phase state of the tissue ablation to a channel phase based on one or more measurements obtained from the measurement devices 124(1)-124(n). In one example, data correlated with a plurality of waveform patterns indicating the tissue ablation voltage and/or current cycle, such as shown in FIG. 6, are stored in the memory 116 of the tissue ablation monitoring computing device 108. If in step 212, the tissue ablation monitoring computing device 108 determines that the threshold has not been exceeded, then the No branch is taken to step 204 where one or more items of data are received and the method is repeated from that step.

If in step 212, the tissue ablation monitoring computing device 108 determines that the threshold has been exceeded indicating a phase state change to a channel phase, then the Yes branch is taken to step 214 where the tissue ablation monitoring computing device 108 is configured to terminate energy delivery based on measured values reaching or exceeding the pre-determined threshold, such as current level, voltage level, power level, impedance level, and/or activation time by way of example only.

Although present disclosure describe using energy therapy to treat vascular occlusion, it is contemplated that various aspects of this technology described herein may be applied to various other therapeutic or cosmetic operations, such as in the field of oncology, electrophysiology, or dermatology by way of example only.

Having thus described the basic concept of the technology, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the technology. Accordingly, the technology is limited only by the following claims and equivalents thereto.

What is claimed is:

1. An apparatus comprising:
    a first longitudinal member and a second longitudinal member configured to be located near a tissue region;
    an energy source coupled to the first longitudinal member and the second longitudinal member;
    a measuring device configured to measure at least one characteristic of the tissue region; and
    an energy controller coupled to the energy source and the measuring device, the energy controller comprising a processor coupled to a memory and configured to execute programmed instructions stored in the memory, comprising:
        initiating a delivery of energy to the tissue region from the energy source;
        receiving one or more items of data from the measuring device based on the delivery of energy to the tissue region;
        determining a pre-plasma phase, a plasma phase, and a channel phase in the tissue region based on the one or more items of data throughout formation of a channel in the tissue region; and
        adjusting the delivery of energy to the tissue region based on the determined pre-plasma phase, plasma phase, and channel phase states throughout the formation of the channel in the tissue region.

2. The apparatus as set forth in claim 1 wherein the processor is further configured to execute programmed instructions stored in the memory further comprising:
    comparing the one or more items of data with one or more parameters related to the one or more items of data; and
    adjusting the delivery of energy to the tissue region based on the comparison.

3. The apparatus as set forth in claim 2 wherein the one or more parameters comprise one or more tissue ablation waveforms.

4. The apparatus as set forth in claim 2 wherein the one or more parameters are input by a user.

5. The apparatus as set forth in claim 1 wherein the energy source comprises a radio frequency energy source.

6. The apparatus as set forth in claim 1 wherein the measuring device measures an electrical characteristic of the tissue region.

7. The apparatus as set forth in claim 6 wherein the electrical characteristic comprises one or more of current, voltage, forward power, reverse power, phase angle, or impedance.

8. The apparatus as set forth in claim 1 wherein the measuring device measures a physiological characteristic of the tissue region.

9. The apparatus as set forth in claim 8 wherein the physiological characteristic comprises one or more or of an impedance, a temperature, a pressure, a composition, or an elasticity.

10. The apparatus as set forth in claim 1 wherein the measuring device measures a visual characteristic of the tissue region.

11. The apparatus as set forth in claim 10 wherein the measuring device comprises one of intravascular ultrasound, optical coherence tomography, optical coherence reflectometry, or angiography.

12. The apparatus as set forth in claim 1 wherein the adjusting the delivery of energy to the tissue region further comprises terminating the energy delivery when the one or more items of data from the measuring device exceed a threshold value.

13. The apparatus as set forth in claim 1 wherein the one or more items of data comprises a voltage waveform and wherein the pre-plasma phase is indicated by a peak voltage measurement of the voltage waveform, the plasma phase is indicated by a decrease in the voltage measurement of the voltage waveform, and the channel phase is indicated by a further decrease in the voltage measurement of the voltage waveform.

14. The apparatus as set forth in claim 1 wherein the one or more items of data comprises a current waveform and wherein the pre-plasma phase is indicated by a minimum current measurement of the waveform, the plasma phase is indicated by an increase in the current measurement of the current waveform, and the channel phase is indicated by a further increase in the current measurement of the current waveform.

15. The apparatus as set forth in claim 1 wherein the adjusting the delivery of energy to the tissue region further comprises adjusting the delivery of energy to minimize treatment time.

16. The apparatus as set forth in claim 1 wherein the adjusting the delivery of energy to the tissue region further comprises adjusting the delivery of energy to minimize thermal effects on the tissue region.

17. A method comprising:
    initiating, by a tissue ablation monitoring computing device, a delivery of energy from an energy source to a tissue region through a first longitudinal member and a second longitudinal member located near the tissue region;
    receiving, by the tissue ablation monitoring computing device, one or more items of data from a measuring device based on the delivery of energy to the tissue region;
    determining, by the tissue ablation monitoring computing device, a pre-plasma phase, a plasma phase, and a channel phase in the tissue region based on the one or more items of data throughout formation of a channel in the tissue region; and
    adjusting, by the tissue ablation monitoring computing device, the delivery of energy to the tissue region based on the determined pre-plasma phase, plasma phase, and channel phase states throughout the formation of the channel in the tissue region.

18. The method as set forth in claim 17 further comprising:
    comparing, by the tissue ablation monitoring computing device, the one or more items of data with one or more parameters related to the one or more items of data; and
    adjusting, by the tissue ablation monitoring computing device, the delivery of energy to the tissue region based on the comparison.

19. The method as set forth in claim 18 wherein the one or more parameters comprise one or more tissue ablation waveforms.

20. The method as set forth in claim 18 wherein the one or more parameters are input by a user.

21. The method as set forth in claim 17 wherein the energy source comprises a radiofrequency energy source.

22. The method as set forth in claim 17 wherein the measuring device measures an electrical characteristic of the tissue region.

23. The method as set forth in claim 22 wherein the electrical characteristic comprises one of current, voltage, forward power, reverse power, phase angle, or impedance.

24. The method as set forth in claim 17 wherein the measuring device measures a physiological characteristic of the tissue region.

25. The method as set forth in claim 24 wherein the physiological characteristic comprises one or more of an impedance, a temperature, a pressure, a composition, or an elasticity.

26. The method as set forth in claim 17 wherein the measuring device measures a visual characteristic of the tissue region.

27. The method as set forth in claim 26 wherein the measuring device comprises one of intravascular ultrasound, optical coherence tomography, optical coherence reflectometry, or angiography.

28. The method as set forth in claim 17 wherein the adjusting the delivery of energy to the tissue region based on the comparison further comprises terminating the energy delivery when the one or more items of data from the measuring device exceed a threshold value.

29. The method as set forth in claim 17 wherein the one or more items of data comprises a voltage waveform and further wherein the pre-plasma phase is indicated by a peak voltage measurement of the voltage waveform, the plasma phase is indicated by a decrease in the voltage measurement of the voltage waveform, and the channel phase is indicated by a further decrease in the voltage measurement of the voltage waveform.

30. The method as set forth in claim 17 wherein the one or more items of data comprises a current waveform and further wherein the pre-plasma phase is indicated by a minimum current measurement of the current waveform, the plasma phase is indicated by an increase in the current measurement of the current waveform, and the channel phase is indicated by a further increase in the current measurement of the current waveform.

31. The method as set forth in claim 17 wherein the adjusting the delivery of energy to the tissue region further comprises adjusting the delivery of energy to minimize treatment time.

32. The method as set forth in claim 17 wherein the adjusting the delivery of energy to the tissue region further comprises adjusting the delivery of energy to minimize thermal effects on the tissue region.

* * * * *

UNITED STATES PATENT AND TRADEMARK OFFICE
CERTIFICATE OF CORRECTION

PATENT NO. : 10,201,383 B2
APPLICATION NO. : 14/216849
DATED : February 12, 2019
INVENTOR(S) : Ogata et al.

Page 1 of 1

It is certified that error appears in the above-identified patent and that said Letters Patent is hereby corrected as shown below:

On the Title Page

Item (71) under the "Applicant" field: delete "RetroVascular, Inc., Pleasanton, CA (US)" and insert -- Asahi Medical Technologies, Inc., Pleasanton, CA (US) --.

Signed and Sealed this
Fourteenth Day of May, 2019

Andrei Iancu
*Director of the United States Patent and Trademark Office*